United States Patent
Tokita

(10) Patent No.: US 9,901,257 B2
(45) Date of Patent: Feb. 27, 2018

(54) OBJECT INFORMATION ACQUIRING APPARATUS AND PHOTOACOUSTIC PROBE

(71) Applicant: CANON KABUSHIKI KAISHA, Tokyo (JP)

(72) Inventor: Toshinobu Tokita, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/051,934

(22) Filed: Oct. 11, 2013

(65) Prior Publication Data

US 2014/0114171 A1   Apr. 24, 2014

(30) Foreign Application Priority Data

Oct. 23, 2012   (JP) .................. 2012-233903

(51) Int. Cl.
   *A61B 5/00* (2006.01)

(52) U.S. Cl.
   CPC .................. *A61B 5/0095* (2013.01)

(58) Field of Classification Search
   CPC .................................................. A61B 5/0095
   See application file for complete search history.

(56) References Cited

U.S. PATENT DOCUMENTS

| | | | |
|---|---|---|---|
| 6,547,721 B1* | 4/2003 | Higuma | A61B 1/121 600/109 |
| 2004/0077949 A1* | 4/2004 | Blofgett | A61B 5/0088 600/472 |
| 2008/0123083 A1* | 5/2008 | Wang | A61B 5/0091 356/73 |
| 2011/0112391 A1 | 5/2011 | Nishihara et al. | 600/407 |
| 2011/0144496 A1* | 6/2011 | Li | A61B 5/0095 600/443 |
| 2011/0245667 A1 | 10/2011 | Tokita | 600/437 |
| 2011/0303015 A1 | 12/2011 | Ichihara et al. | 73/656 |
| 2012/0150012 A1 | 6/2012 | Fujimoto et al. | 600/407 |

(Continued)

FOREIGN PATENT DOCUMENTS

| | | |
|---|---|---|
| JP | H01-148245 | 6/1989 |
| JP | 2010-017426 | 1/2010 |

(Continued)

OTHER PUBLICATIONS

S. Ermilov et al., "Development of Laser Optoacoustic and Ultrasonic Imaging System for Breast Cancer Utilizing Handheld Array Probes", *Photons Plus Ultrasound: Imaging and Sensing, Proc. of SPIE*, vol. 7177, pp. 717703-1 et seq. (2009).

(Continued)

*Primary Examiner* — Long V Le
*Assistant Examiner* — Colin T Sakamoto
(74) *Attorney, Agent, or Firm* — Fitzpatrick, Cella, Harper & Scinto

(57) ABSTRACT

There is provided an object information acquiring apparatus that includes: an optical system forming light from a light source; an emission end emitting the light; a diffuser panel diffusing the emitted light; a spacer defining a distance between the diffuser panel and an object; a receiver receiving an acoustic wave generated from the object to which the light is emitted; and a processor acquiring information on inside of the object on the basis of the acoustic wave.

23 Claims, 6 Drawing Sheets

(56) References Cited

U.S. PATENT DOCUMENTS

| | | | |
|---|---|---|---|
| 2012/0238859 A1 | 9/2012 | Tokita et al. | 600/407 |
| 2012/0302865 A1 | 11/2012 | Tokita et al. | 600/407 |
| 2013/0167648 A1 | 7/2013 | Tokita | 73/655 |
| 2013/0261426 A1* | 10/2013 | Irisawa | A61B 5/0095 600/407 |
| 2013/0301380 A1* | 11/2013 | Oraevsky | A61B 8/5215 367/7 |
| 2014/0051971 A1 | 2/2014 | Tokita | 600/407 |
| 2014/0114170 A1 | 4/2014 | Tokita et al. | 600/407 |

FOREIGN PATENT DOCUMENTS

| | | |
|---|---|---|
| JP | 2010-167167 | 8/2010 |
| JP | 2011-255028 | 12/2011 |
| JP | 2012-135427 | 7/2012 |
| JP | 2012-170762 | 9/2012 |
| WO | WO 2011135820 A1 * | 11/2011 |
| WO | WO 2012108171 A1 * | 8/2012 |

OTHER PUBLICATIONS

JPO Office Action issued on Aug. 31, 2016, in counterpart Japanese patent application 2012-233903, with translation.
JPO Office Action issued on Mar. 21, 2017, in counterpart Japanese patent application 2012-233903, with partial translation.

* cited by examiner

OBJECT INFORMATION ACQUIRING APPARATUS AND PHOTOACOUSTIC PROBE

BACKGROUND OF THE INVENTION

Field of the Invention

The present invention relates to an object information acquiring apparatus and a photoacoustic probe.

Description of the Related Art

As a method of specifically imaging vascularization caused by cancer, photoacoustic tomography (hereinafter, PAT) has been attracting attention. The PAT is a system of illuminating an object with illumination light (near-infrared rays), and receiving a photoacoustic wave generated from the inside of the object with an ultrasound probe to image.

FIG. 4 is a schematic diagram of a handheld photoacoustic apparatus described in "S. A. Ermilov et al., Development of laser optoacoustic and ultrasonic imaging system for breast cancer utilizing handheld array probes, Photons Plus Ultrasound: Imaging and Sensing 2009, Proc. of SPIE vol. 7177, 2009". A photoacoustic probe 104 has a structure in which a receiver 106 for receiving a photoacoustic wave is sandwiched between illumination optical systems including emission ends 103b of a bundle fiber 103 to be fixed. Illumination light from a light source 101 enters the bundle fiber 103 from an incident end 103a to be applied to an object from the emission ends 103b. Then, the receiver 106 receives a photoacoustic wave generated from the object by a photoacoustic effect to convert the generated photoacoustic wave into an electric signal. A processor 107 of an ultrasound apparatus 109 amplifies or digitalizes the electric signal, or performs image reconstruction the electric signal, so that image information (IMG) is generated to be transmitted to a display apparatus 108. Consequently, a photoacoustic image that indicates characteristic information on the inside of the object is displayed.

Non Patent Literature 1: S. A. Ermilov et al., Development of laser optoacoustic and ultrasonic imaging system for breast cancer utilizing handheld array probes, Photons Plus Ultrasound: Imaging and Sensing 2009, Proc. of SPIE vol. 7177, 2009.

SUMMARY OF THE INVENTION

However, the conventional technique has the following problems.

In FIG. 4, the bundle fiber 103 is used for optical transmission from the light source 101 to the emission ends 103b. However, the bundle fiber 103 is manufactured by making fiber element wires of about 200 μm into a bundle, and therefore light generated from each fiber interferes with light generated from other fibers, and an energy density sometimes locally becomes higher.

Furthermore, an energy density varies according to the distances from the emission ends of the bundle fiber, and the shorter the distance is, the higher the energy density tends to locally become. Therefore, the energy density sometimes becomes higher also by deformation of the object. Herein, as the safety standards, maximum permissible exposure (MPE) to skin is stipulated in "ANSI 2136. 1-2000". However, for example, in a case where an object is a human body, there is a possibility that an energy density locally becomes higher, and exceeds the MPE, when illumination light is applied to a skin surface. Therefore, there is room for improvement of safety.

Additionally, unlike the "S. A. Ermilov et al., Development of laser optoacoustic and ultrasonic imaging system for breast cancer utilizing handheld array probes, Photons Plus Ultrasound: Imaging and Sensing 2009, Proc. of SPIE vol. 7177, 2009", even in a case where optical transmission is performed by using a mirror or a reflecting prism in place of the bundle fiber 103, and, the uneven beam profile of the light source 101 is directly applied to the object, and therefore an energy density sometimes locally becomes higher. Therefore, there is room for improvement of safety for optical transmission without the bundle fiber 103.

The present invention has been conceived in order to solve the aforementioned problems, and the object thereof is to suppress local increase in an energy density at the time of light irradiation with photoacoustic tomography.

The present invention provides an object information acquiring apparatus comprising:

an optical system configured to form light from a light source;

an emission end configured to emit the light;

a diffuser panel configured to diffuse the emitted light;

a spacer configured to define a distance between the diffuser panel and an object;

a receiver configured to receive an acoustic wave generated from the object to which the light is emitted; and a processor configured to acquire information on inside of the object on the basis of the acoustic wave.

The present invention also provides a photoacoustic probe comprising:

an optical system configured to form light from a light source;

an emission end configured to emit the light;

a diffuser panel configured to diffuse the light that is emitted;

a spacer configured to define a distance between the diffuser panel and an object; and a receiver configured to receive an acoustic wave generated from the object to which the light is emitted.

According to the present invention, it possible to suppress local increase in an energy density at the time of light irradiation with photoacoustic tomography.

Further features of the present invention will become apparent from the following description of exemplary embodiments with reference to the attached drawings.

DESCRIPTION OF THE EMBODIMENTS

Hereinafter, a preferred embodiment of the present invention will be described with reference to the drawings. However, size, quality of materials, shape, relative arrangement of components described below should be appropriately changed according to a configuration of an apparatus to which the invention is applied, or various conditions, and the scope of this invention is not limited to the description as below.

An object information acquiring apparatus of the present invention includes an apparatus which utilizes a photoacoustic effect of receiving an acoustic wave generated inside an object by applying light (electromagnetic wave) to the object, and acquiring object information as image data. The object information indicates a generation source distribution of acoustic waves generated by light application, or an initial sound pressure distribution of the inside of the object, an optical energy absorption density distribution or an absorption coefficient distribution derived from the initial sound pressure distribution, or a concentration distribution of substances configuring tissues. Examples of the concentration distribution of substances include an oxygen saturation distribution, an oxygenated/reduced hemoglobin concentration distribution, and the like, for example.

An acoustic wave in the present invention is typically an ultrasound wave, and includes an elastic wave referred to as a sound wave, an ultrasound wave, or an acoustic wave. An acoustic wave generated by a photoacoustic effect is referred to as a photoacoustic wave, or a light-induced ultrasound wave.

Figure 1:
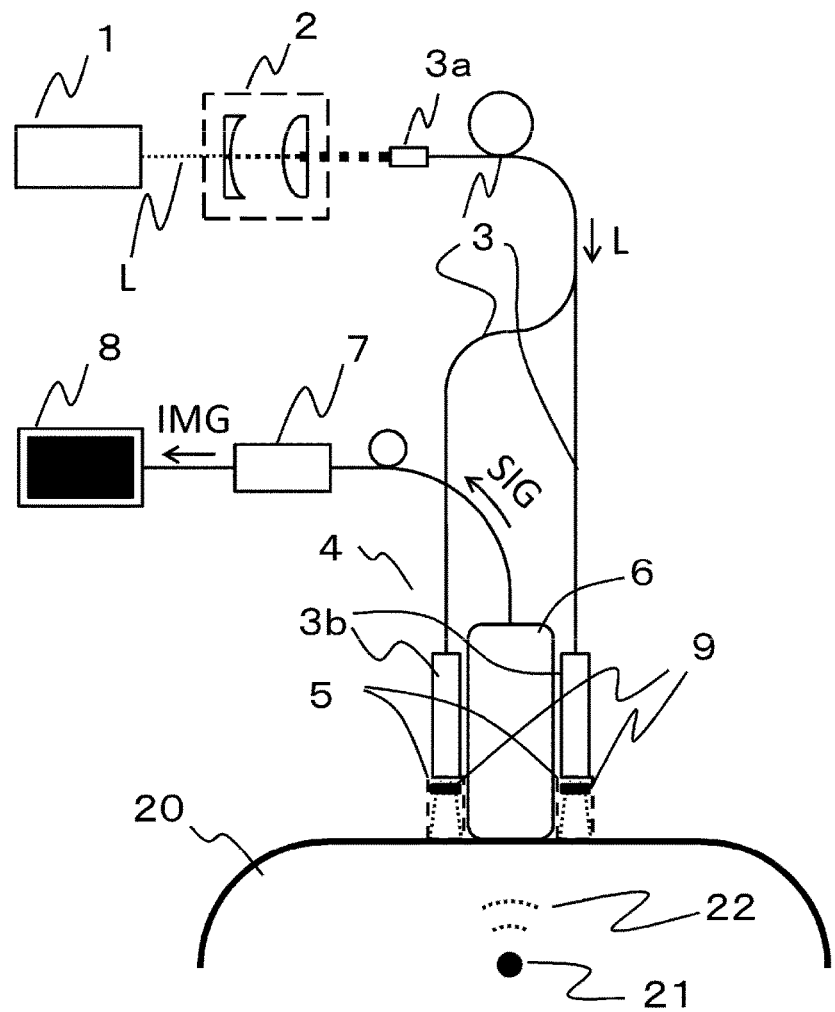
FIG. 1 is a figure for illustrating a configuration of a photoacoustic apparatus according to an embodiment of the present invention.

The embodiment of the present invention will be described with reference to FIG. 1. FIG. 1 schematically shows a photoacoustic apparatus. In the photoacoustic apparatus, illumination light L emitted from a light source 1 is formed by a first illumination optical system 2 to enter an incident end 3a of a bundle fiber 3. The illumination light L is transmitted to a photoacoustic probe 4 by the bundle fiber 3 to be emitted from emission ends 3b of the bundle fiber 3. The bundle fiber is also referred to as an optical transmission unit.

The photoacoustic probe 4 is configured from emission ends 3b, second illumination optical systems 5 that form illumination light emitted from the emission ends 3b, and a receiver 6 that receives a photoacoustic wave. When illumination light that reaches an object 20 through the second illumination optical systems 5 is diffused and propagated inside the object to be absorbed in an absorber 21, a photoacoustic wave 22 is generated. Note that the first and second illumination optical systems each have a function of forming illumination light, and can be considered as an optical system of an apparatus by uniting these.

The receiver 6 includes an element that converts an acoustic wave and an electric signal, such as a piezoelectric element or a CMUT. Therefore, when the receiver 6 receives the photoacoustic wave 22 that is propagated in the object 20, the photoacoustic wave 22 is converted into an electric signal SIG by the element. Thereafter, after amplification, digital transform, filtering processing, and the like are performed to the electric signal SIG that is transmitted to a processor 7, image reconstruction is performed by a known method, thereby generating image information IMG. The image information IMG is transmitted to a display apparatus 8, and the information on the inside of the object is displayed.

Herein, in the present invention, the second illumination optical systems 5 are provided with diffuser panels 9. The diffuser panels 9 are each placed at a prescribed distance from an object. This prescribed distance is determined from optical energy, coherency of light, and an irradiation area to the object.

The optical energy is a total amount of light emitted from the emission ends 3b. The coherency of light results from the position and the size of each emission end 3b, the core diameter and the fiber diameter of each of the fiber element wires of the bundle fiber 3, and bundle density of the fiber element wire, and the diffusion angle of each diffuser panel 9. The irradiation area to the object is determined from an area that is expanded such that the total amount of emitted light is at most maximum permissible exposure to skin.

For example, when a distance between each diffuser panel 9 and the object is 7 mm or more, it is possible to suppress the local increase in the distribution of energy densities. The condition at this time will be indicated as follows.

The optical energy is 60 mJ. As to coherency, the distance from the object to the emission ends 3b is 9 mm, and the size of the emission ends 3b is 30 mm×1.4 mm×2 locations, the core diameter of the fiber element wire is 190 μm, the fiber diameter of the fiber element wire is 200 μm, the bundle is roughly provided in a hexagonal close-packed lattice pattern. As each diffuser panel 9, a holographic diffuser with a diffusion angle of 10° is used. The irradiation area is about 35 mm×6 mm×2 locations.

Under the above condition, light is applied to the object at a wavelength of 756 nm, and a light emission frequency of 10 Hz, and the optical energy density is measured. As a result, it is possible to obtain an optical energy density of about 20 mJ/cm$^2$ at most, which is smaller than 26 mJ/cm$^2$ that is the maximum permissible exposure MPE.

In FIG. 1, the bundle fiber 3 branches in the middle, and the two emission ends 3b of the bundle fiber 3 and the two second illumination optical systems 5 are provided. However, the number of branches is not limited to this. For example, it is effective that the bundle fiber is located adjacent to one surface of the receiver 6 without branching. On the contrary, the number of branches may be greater than two.

The photoacoustic probe 4 is preferably covered with a housing.

The light source 1 preferably emits near-infrared rays with wavelengths of about 600 nm to 1100 nm. As the light source 1, for example, a pulse laser such as a Nd:YAG laser and an alexandrite laser, or a Ti:sa laser or an OPO laser using the Nd:YAG laser light as excitation light, a semiconductor laser, or the like can be utilized.

Figure 5:
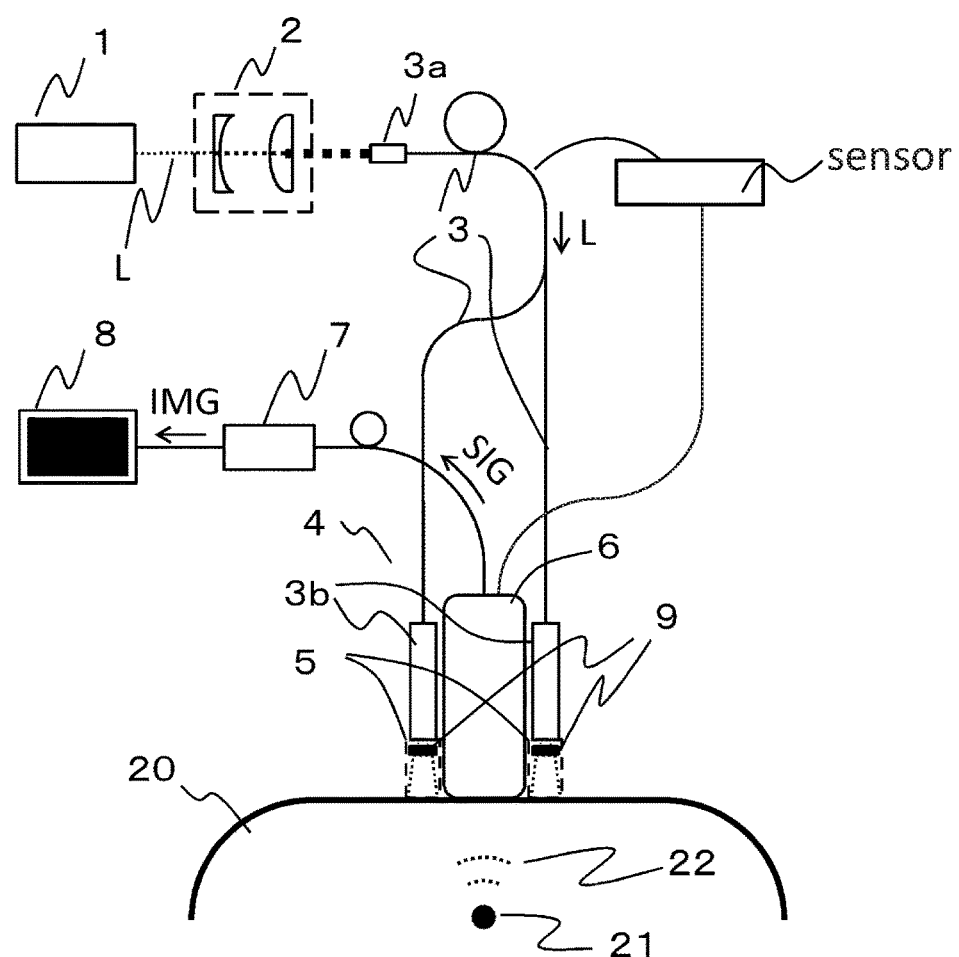
FIG. 5 is a figure illustrating a further configuration of a photoacoustic apparatus according to one practical example.
Figure 6:
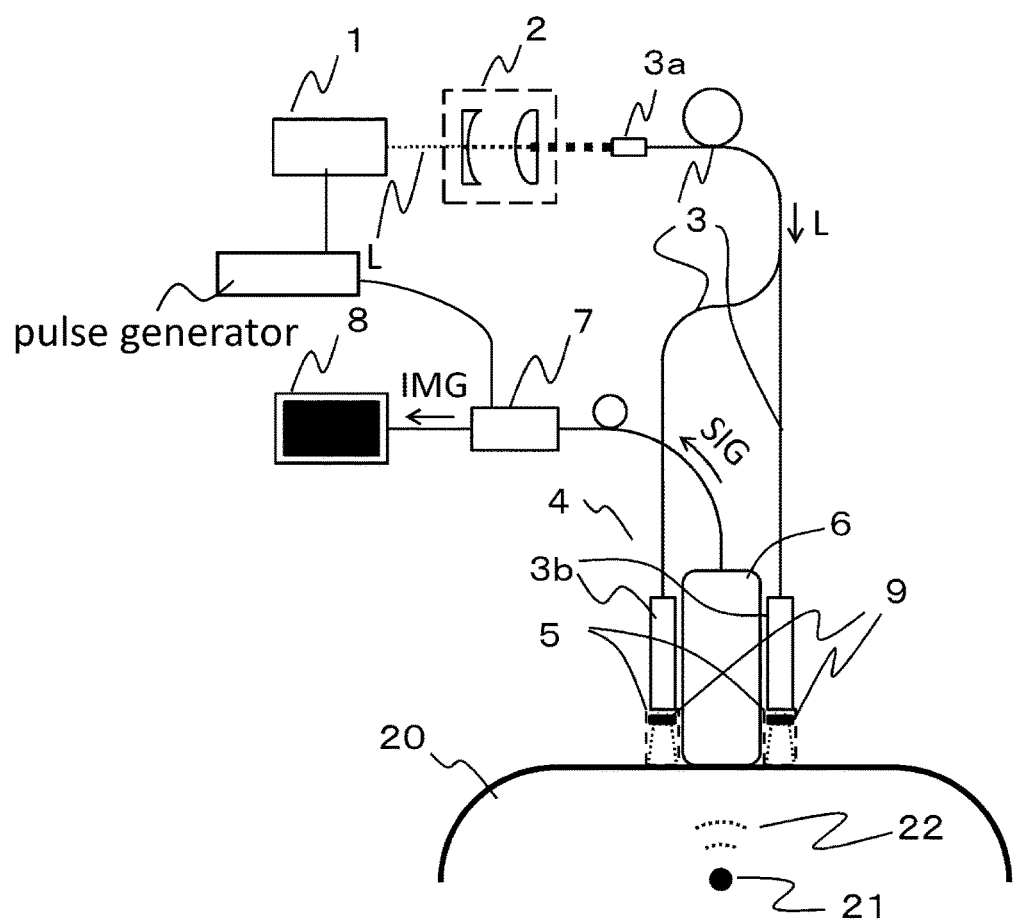
FIG. 6 is a figure illustrating a variation of the photoacoustic apparatus of FIG. 5.

It is necessary to synchronize the irradiation of illumination light and the reception of a photoacoustic wave by the receiver 6. Therefore, an optical path between the light source 1 and each second illumination optical system 5 may be partially branched, and light may be detected by a sensor such as a photodiode (see FIG. 5), and the receiver 6 may be caused to start receiving by a trigger of the detection signal. Alternatively, a pulse generator (see FIG. 6) may control such that the light emission timing of the light source 1 and the reception timing of the processor 7 may be synchronized.

According to the above configuration, it is possible to suppress the local increase in the energy density distribution of illumination light applied to an object. Therefore, the safety of an apparatus can be improved.

<First Practical Example>

Figure 2A:
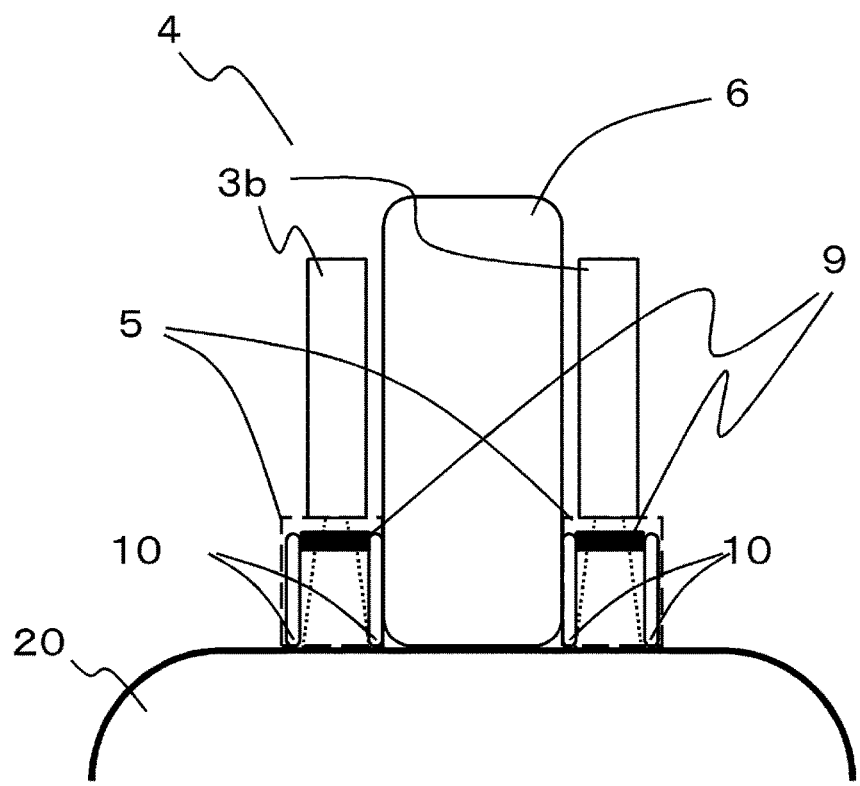
FIG. 2A and FIG. 2B are each a figure for illustrating a photoacoustic probe according to a first practical example.

In this practical example, the photoacoustic probe 4 will be more specifically described with reference to FIG. 2A and FIG. 2B. FIG. 2A is a front view/sectional view of the photoacoustic probe 4, and FIG. 2B is a bottom view.

In this practical example, spacers 10 are provided in the second illumination optical systems 5 so as to define the distances between the diffuser panels 9 and the object 20. Furthermore, the spacers 10 are surrounded by illumination light, and the distal ends thereof are provided so as to roughly flush with the reception surface of the receiver 6.

Figure 2B:
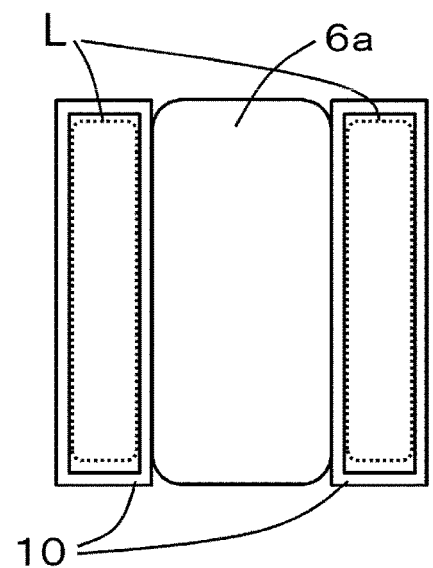

FIG. 2A shows cross-sections of the spacers 10, and FIG. 2B, which is a bottom view, shows spacers 10, the reception surface 6a of the receiver 6, and illumination light L, as viewed from the side of the object 20.

The materials of the spacers are preferably materials that have stiffness sufficiently higher than an object, for example, metal such as aluminum, various plastic resin, or ceramics, so as not to deform due to contact with the object.

In this practical example, the irradiation region of illumination light is 35 mm×7 mm×2 (both side of the receiver 6), and the spacers 10 made of aluminum are provided on outer periphery of about 0.5 mm. The distances between the diffuse surfaces of the diffuser panels 9 and the surfaces of the spacers 10 are each 8 mm at the shortest.

Under such a condition, the maximum value of an energy density obtained when energy of 120 mJ is emitted from the light source 1 is 18 mJ/cm$^2$. When pressing against the object, the photoacoustic probe 4 does not enter the inside with respect to the surfaces of the spacers 10 by 1 mm at most regardless of the pressing manner, and the maximum value of the energy density is hardly changed.

Edge portions of the surfaces of the spacers 10, which are in contact with the object, are preferably moderately rounded, and the rounds are each defined as R0.5 in the first practical example. With such a configuration, when the photoacoustic probe 4 is pressed against the object, no pain is felt, and no cut is got. The edge portions may be provided with C chamfers in place of the rounds.

As described above, in a case where an object is a biological body, even if the object is deformed when the photoacoustic probe 4 is pressed against the object, the distances between the object and the diffuser panels 9 can be defined by the spacers 10. Therefore, the change in the energy density distribution of illumination light applied to the object is small, and a stable illumination distribution is obtained.

When a distribution of light that enters inside an object is calculated on the basis of a light diffusion equation, the change in a light distribution of the object surface, which serves as a boundary condition, can be reduced, and the light distribution of the inside of the object can be calculated with higher accuracy. As a result, an absorption coefficient of an absorber inside the object $\mu_a = p/(\Gamma\phi)$ (p: initial sound pressure, $\Gamma$: Grueneisen coefficient, $\phi$: light amount of the absorber) can be calculated with high accuracy. The initial sound pressure p is obtained from a photoacoustic signal measured by the receiver 6. The Grueneisen coefficient $\Gamma$ is a known value, and is about 0.5 to 0.8, in a case where an object is, for example, a human breast.

<Second Practical Example>

Figure 3A:
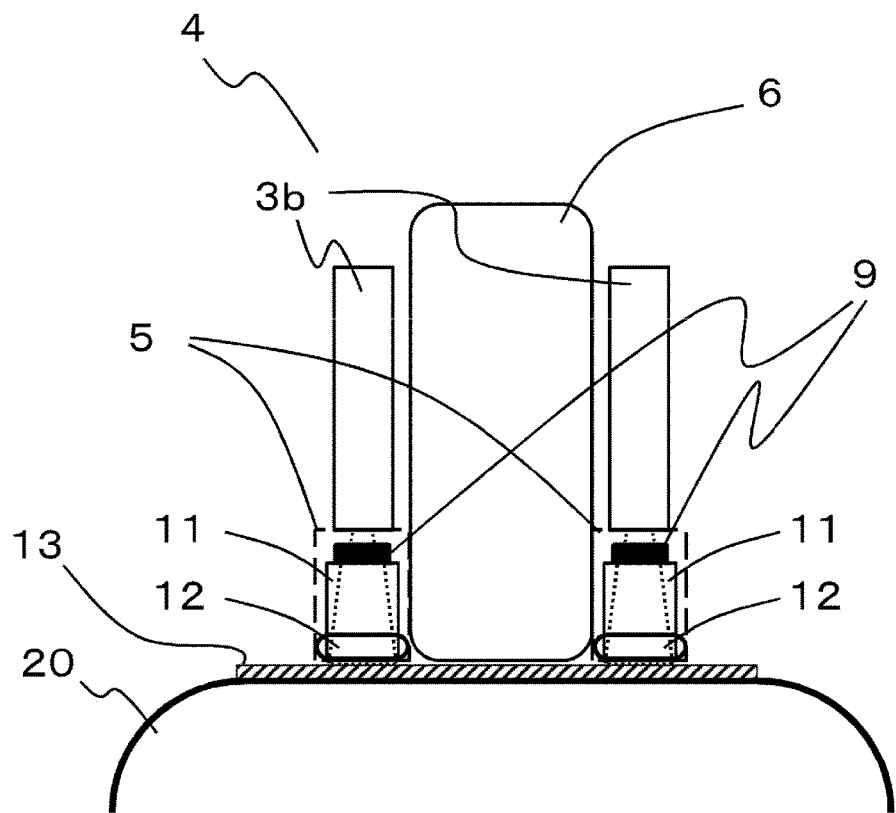
FIG. 3A and FIG. 3B are each a figure for illustrating a photoacoustic probe according to a second practical example.
Figure 3B:
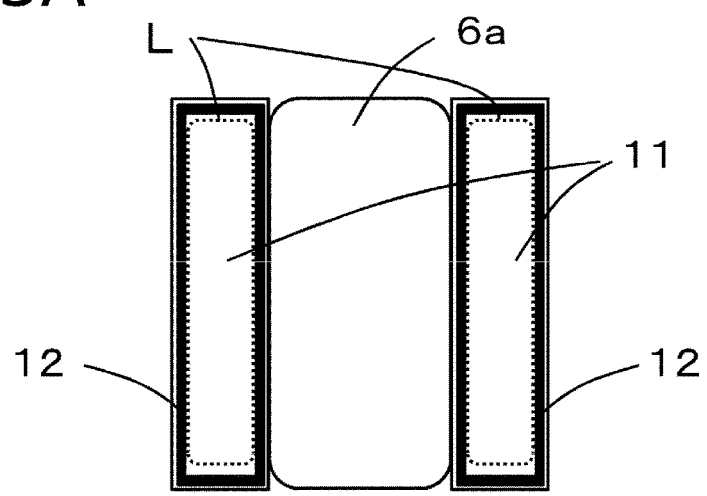
Figure 4:
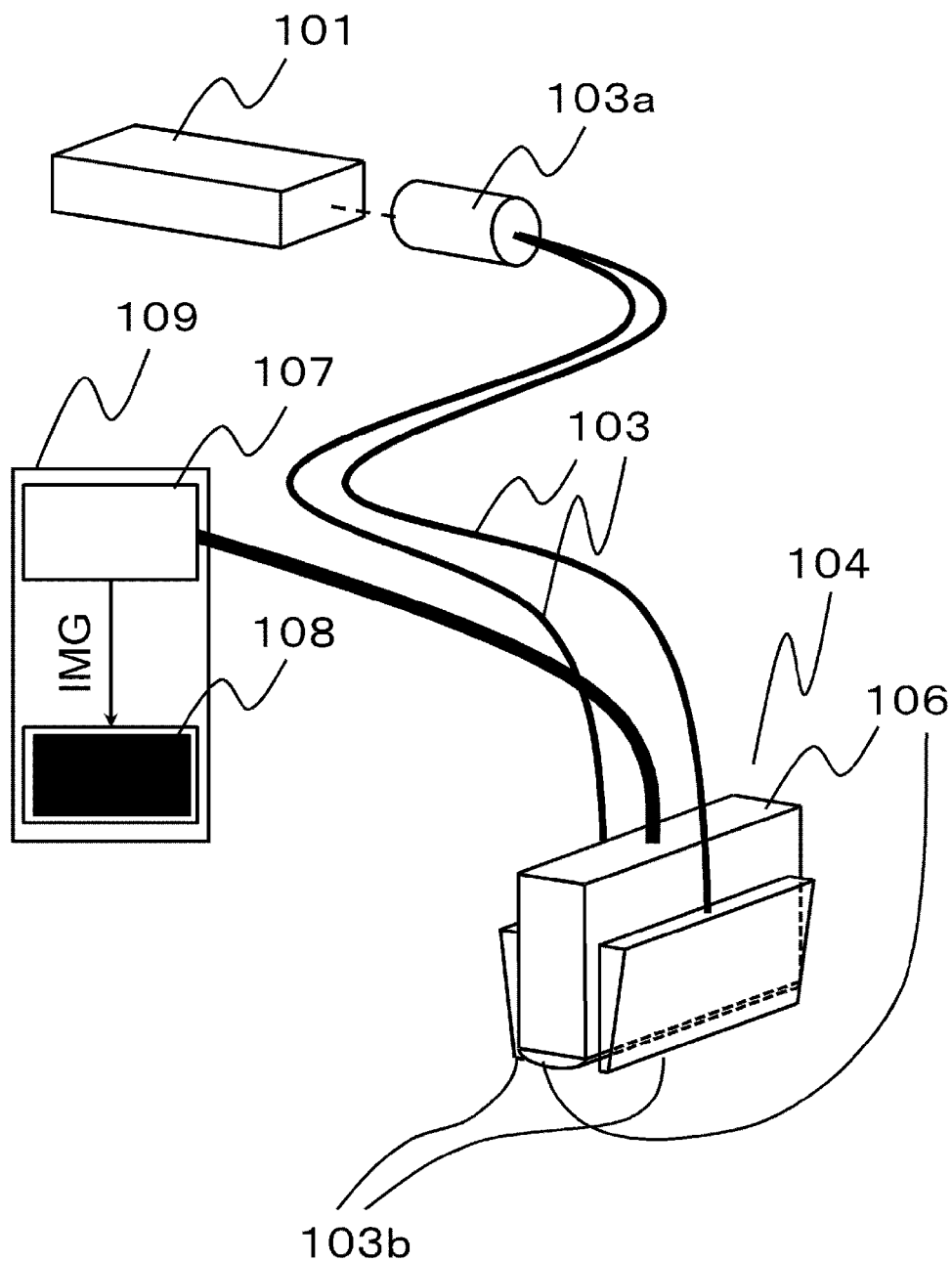
FIG. 4 is a figure for illustrating a configuration of a photoacoustic apparatus of a background technology.

In this practical example, a photoacoustic probe 4 that is different from the photoacoustic probe of the first practical example will be more specifically described with reference to FIG. 3A and FIG. 3B. FIG. 3A is a front view of the photoacoustic probe 4, and FIG. 3B is a bottom view.

In this practical example, transparent bodies 11 are provided in the second illumination optical systems 5 as spacers. Consequently, an effect of defining distances between the diffuser panels 9 and the object 20 is obtained similarly to the spacers 10 described in the first practical example. At this time, as shown in FIG. 3B, the transparent bodies 11 are provided so as to surround light, but may extend so as to cover contact surfaces with the object. In such a case, transparent bodies 11 are each a three-dimensional shape in which the surface on the side of an emission end 3b is opened.

Generally, when the photoacoustic apparatus is used, sonar gel 13 is used on a portion where the receiver 6 is in contact with the object (reception surface 6a), for acoustic matching. When the sonar gel 13 is adhered to the diffuse surfaces of the diffuser panels 9, the diffusion angle changes, and therefore the energy density distribution where light is applied to the object changes. The acoustic matching material of the photoacoustic probe and the object is not limited to the sonar gel, and for example, water can be used.

However, when the transparent bodies 11 cover also the contact surfaces with an object, it is possible to prevent the entry of sonar gel in the second illumination optical systems 5, and to suppress adhering to the diffuser panels 9. As shown in FIG. 3B, sealing members 12 surround the peripheries of the transparent bodies 11, thereby enhancing this entry suppression effect. That is, it is possible to suppress the adhering of sonar gel to the diffuse surfaces of the diffuser panels 9, and the energy density distribution where light is applied to an object can be kept constant.

Furthermore, a portion to which sonar gel is adhered is limited to a portion where the photoacoustic probe 4 is in contact with an object, as shown in FIG. 3B. Therefore, after the photoacoustic apparatus is used, sonar gel can be easily wiped off, and the sanitary condition of the photoacoustic probe 4 can be favorably kept.

As the transparent bodies 11, prisms or slide glasses can be utilized. The quality of the material is not limited to glasses, and optical materials such as acryl and polycarbonate are also applicable.

The transparent bodies 11 are shown in the figures so as to be in contact with the object and the diffuser panels 9, but are not limited to this. It is effective that the transparent bodies 11 are provided to be separated from the object and the diffuser panels 9.

For the sealing members 12, O-rings, rubber packing, gaskets, or adhesives is applicable.

In the above practical examples, a bundle fiber is used as the optical transmission unit. However, the optical transmission unit is not actually limited to this, and for example, a mirror or a reflecting prism can be used. Also in such a case, the diffuser panels 9 are each provided to be separated from the object 20 by a prescribed distance or more in order to make illumination light even. In this time, the spacers 10 described in the first practical example, or the transparent bodies 11 described in the second practical example are preferably provided between the diffuser panels 9 and the object 20 to define the distances between both.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-233903, filed on Oct. 23, 2012, which is hereby incorporated by reference herein in its entirety.

What is claimed is:

1. An object information acquiring apparatus comprising:
   an optical system configured to form light from a light source;
   an emission end configured to emit the light that has exited from the optical system;
   a diffuser panel configured to diffuse the emitted light;
   a spacer arranged with its relative position to said diffuser panel fixed, said spacer spanning a distance from said diffuser panel to a position for an object;

a receiver having a receiving surface configured to receive an acoustic wave generated from the object to which the light is emitted; and a processor configured to acquire information on inside of the object on the basis of the acoustic wave, wherein the spacer is located in front of the diffuser panel, as seen from the position for the object, and is not located in front of the receiving surface, such that the receiving surface is located closer to the position for the object than the diffuser panel is.

2. The object information acquiring apparatus according to claim 1, further comprising the light source, wherein said light source is configured to output the light in pulses of an energy, up to a maximum time of outputting of the light, wherein said light source has a maximum power setting, and wherein said spacer defines the distance between said diffuser panel and the object such that a total energy of emitted light emitted from said emission end and delivered to the object during emission of the light during the maximum time is at most a product of a maximum permissible exposure of skin to the emitted light and a total irradiation area on which the object receives the light.

3. The object information acquiring apparatus according to claim 1, wherein said spacer is configured to surround the light emitted from said emission end.

4. The object information acquiring apparatus according to claim 3, wherein said spacer is made of a transparent material.

5. The object information acquiring apparatus according to claim 1, wherein the irradiation of the illumination light from said emission end to the object and the reception of the acoustic wave from the object by said receiver are performed synchronously.

6. The object information acquiring apparatus according to claim 5, further comprising a pulse generator, wherein the irradiation of the illumination light and the reception of the acoustic wave are synchronized by said pulse generator.

7. The object information acquiring apparatus according to claim 5, further comprising a sensor for detecting light,
wherein an optical path between said light source and said emission end is branched into a first optical path and a second optical path,
said emission end is provided on said first optical path to emit light to the object via said diffuser plate,
said second optical path is configured to emit light to said sensor, and
said receiver is configured to start receiving the acoustic wave when said sensor detects light.

8. The object information acquiring apparatus according claim 1, further comprising a seal member arranged on a periphery of said spacer.

9. The object information acquiring apparatus according to claim 8, wherein said seal member has at least one of an O-ring, rubber packing, a gasket, and an adhesive.

10. The object information acquiring apparatus according to claim 1, wherein said optical system comprises a bundle fiber for transmitting the light from the light source.

11. The object information acquiring apparatus according to claim 2, wherein said optical system irradiates said diffuser panel with light having a light profile having energy density more than the maximum permissible exposure.

12. The object information acquiring apparatus according to claim 2, wherein said optical system comprises a bundle fiber for transmitting the light from said light source and irradiating said diffuser panel with light having a light profile having energy density more than the maximum permissible exposure.

13. A photoacoustic probe comprising:
an optical system configured to form light from a light source;
an emission end configured to emit the light that has exited from the optical system;
a diffuser panel configured to diffuse the light that is emitted;
a spacer arranged with its relative position to said diffuser panel fixed, said spacer spanning a distance from said diffuser panel to a position for an object; and
a receiver having a receiving surface configured to receive an acoustic wave generated from the object to which the light is emitted,
wherein the spacer is located in front of the diffuser panel, as seen from the position for the object, and is not located in front of the receiving surface, such that the receiving surface is located closer to the position for the object than the diffuser panel is.

14. An object information acquiring apparatus comprising:
an optical system configured to form light from a light source;
an emission end configured to emit the light that has exited from the optical system;
a diffuser panel configured to diffuse the emitted light;
a spacer provided between said diffuser panel and a position for an object, said spacer spanning the distance from said diffuser panel to the position for the object, and having a contact surface to contact the object in said position when measuring the object;
a receiver having a receiving surface configured to receive an acoustic wave generated from the object to which the light is emitted;
a processor configured to acquire information about inside of the object on the basis of the acoustic wave; and
a signal channel connecting said receiver and said processer,
wherein said optical system comprises a bundle fiber for transmitting the light from the light source, and wherein said signal channel is shorter than said bundle fiber, and
wherein the spacer is located in front of the diffuser panel, as seen from the position for the object, and is not located in front of the receiving surface, such that the receiving surface is located closer to the position for the object than the diffuser panel is.

15. The object information acquiring apparatus according to claim 14, wherein said spacer is arranged with its relative position relative to said diffuser panel fixed.

16. An object information acquiring apparatus comprising:
an optical system having a lens configured to form a light beam from light generated by a light source;
a light guide configured to guide the light beam that has exited from the optical system, the light guide having an emission end configured to emit light;
a diffusion member configured to diffuse the emitted light from the light guide;
a transparent spacer that includes a transparent member having a diffusion member side end and an object side end configured to irradiate the object with the diffused light via the transparent member and via acoustic matching gel provided on the object, the spacer spanning a distance from said diffuser panel to a position for the object;

a receiver having a receiving end configured to face the object and receive an acoustic wave generated at and propagated from the object via the acoustic matching gel;

a housing surrounding the diffusion member and the transparent spacer;

a sealing member arranged on a periphery of the transparent spacer and so as to seal between the housing and the transparent spacer to prevent the acoustic matching gel from penetrating inside of the housing; and a processor configured to acquire information on an inside of the object on the basis of the acoustic wave, wherein the transparent spacer has a spacing length between the diffusion member side end and the object side end such that the object side end of the transparent spacer and the receiving end of the receiver are configured to abut the object via the acoustic matching gel.

17. The object information acquiring apparatus according to claim 16, wherein said sealing member has at least any one of an O-ring, rubber packing, a gasket, and an adhesive.

18. The object information acquiring apparatus according to claim 16, wherein the irradiation of the illumination light from said emission end to the object and the reception of the acoustic wave from the object by said receiver are performed synchronously.

19. The object information acquiring apparatus according to claim 18, further comprising a pulse generator, wherein the irradiation of the illumination light and the reception of the acoustic wave are synchronized by said pulse generator.

20. The object information acquiring apparatus according to claim 18, further comprising a sensor for detecting light, wherein an optical path between said light source and said emission end is branched into a first optical path and a second optical path, said emission end is provided on said first optical path to emit light to the object via said diffuser plate, said second optical path is configured to emit light to said sensor, and said receiver is configured to start receiving the acoustic wave when said sensor detects light.

21. The object information acquiring apparatus according to claim 16, further comprising:

a signal channel connecting said receiver and said processer, wherein said optical system comprises a bundle fiber for transmitting the light from the light source, and wherein said signal channel is shorter than said bundle fiber.

22. The object information acquiring apparatus according to claim 21, wherein said spacer is arranged with its relative position relative to said diffusion member fixed.

23. The object information acquiring apparatus according to claim 16, wherein the object side end and the receiving end are arranged in a coplanar relationship.

* * * * *